United States Patent
Rowland

(10) Patent No.: US 12,272,447 B2
(45) Date of Patent: Apr. 8, 2025

(54) METHOD AND SYSTEM TO FACILITATE PROVISIONING OF AN EMERGENCY HEALTH SERVICE

(71) Applicant: Aneetrai Latoya Rowland, New Haven, CT (US)

(72) Inventor: Aneetrai Latoya Rowland, New Haven, CT (US)

(*) Notice: Subject to any disclaimer, the term of this patent is extended or adjusted under 35 U.S.C. 154(b) by 274 days.

(21) Appl. No.: 17/937,164

(22) Filed: Sep. 30, 2022

(65) Prior Publication Data

US 2023/0101506 A1 Mar. 30, 2023

Related U.S. Application Data

(60) Provisional application No. 63/250,677, filed on Sep. 30, 2021.

(51) Int. Cl.
*G16H 40/20* (2018.01)
*G06Q 50/40* (2024.01)
*G16H 10/60* (2018.01)

(52) U.S. Cl.
CPC ............ *G16H 40/20* (2018.01); *G06Q 50/40* (2024.01); *G16H 10/60* (2018.01)

(58) Field of Classification Search
CPC ......... G16H 40/20; G16H 10/60; G06Q 50/40
See application file for complete search history.

(56) References Cited

U.S. PATENT DOCUMENTS

| | | | |
|---|---|---|---|
| 6,927,694 B1 * | 8/2005 | Smith | B60K 28/066 340/576 |
| 7,254,439 B2 * | 8/2007 | Misczynski | A61B 5/05 340/576 |
| 7,427,924 B2 * | 9/2008 | Ferrone | B60K 28/066 180/274 |
| 7,912,736 B2 | 3/2011 | Wyatt | |
| 7,979,173 B2 * | 7/2011 | Breed | G08G 1/163 701/23 |
| 8,725,311 B1 * | 5/2014 | Breed | A61B 5/11 701/1 |

(Continued)

FOREIGN PATENT DOCUMENTS

| WO | WO-2016079552 A1 * | 5/2016 | ........... G06F 19/327 |
|---|---|---|---|
| WO | WO-2019068616 A1 * | 4/2019 | ......... G06F 21/6218 |
| WO | WO-2019203804 A1 * | 10/2019 | |

OTHER PUBLICATIONS

Kumar, Elsevier, 2015, pp. 1-13.*
(Continued)

*Primary Examiner* — Michael I Ezewoko

(57) ABSTRACT

The present invention connects patients with nearby health care providers by receiving patient information such as name, address, phone number and email. The information is then transmitted to a medical facility that can provide care. The medical facility information is then sent to the processing device for analyzation. The patient is then matched with a primary medical facility and receives a notification. The notification provides the patient with the location directions to the primary medical facility and the estimated wait time before the patient will be seen by a medical professional. For low-income patients a convenient and low-priced form of transportation will be provided picking the patient up and transporting the patient to the primary medical facility.

17 Claims, 11 Drawing Sheets

(56) References Cited

U.S. PATENT DOCUMENTS

| | | | | |
|---|---|---|---|---|
| 9,142,127 | B1* | 9/2015 | McDevitt-Pimbley | G08G 1/052 |
| 9,157,752 | B1* | 10/2015 | Fernández García et al. | B60R 25/30 |
| 9,599,986 | B1* | 3/2017 | Eberbach | B60W 60/007 |
| 9,747,793 | B1* | 8/2017 | Li | G08G 1/095 |
| 9,911,084 | B2* | 3/2018 | Bryson | G01C 21/206 |
| 9,945,679 | B2* | 4/2018 | Bender | G01C 21/3484 |
| 10,007,263 | B1* | 6/2018 | Fields | G06Q 30/0217 |
| 10,266,180 | B1* | 4/2019 | Fields | G08B 25/10 |
| 10,393,532 | B2* | 8/2019 | Foreman | G08G 1/205 |
| 10,595,175 | B2* | 3/2020 | Ramalho de Oliveira | G08G 1/0112 |
| 10,688,867 | B2* | 6/2020 | Wilson | A61B 5/6893 |
| 10,921,812 | B2* | 2/2021 | Wilson | G06Q 10/047 |
| 10,953,888 | B2* | 3/2021 | Wilson | A61B 5/6802 |
| 11,067,985 | B2* | 7/2021 | Kozloski | G05D 1/0223 |
| 11,099,571 | B2* | 8/2021 | Rakshit | A61B 5/18 |
| 11,443,394 | B2* | 9/2022 | Trim | G06Q 90/205 |
| 11,505,117 | B2* | 11/2022 | Lujan | B60W 30/10 |
| 11,615,288 | B2* | 3/2023 | Ceulemans | G06N 3/042 706/14 |
| 11,990,230 | B2* | 5/2024 | Pierson | G08B 25/016 |
| 2006/0200008 | A1* | 9/2006 | Moore-Ede | B60K 28/06 128/920 |
| 2010/0100510 | A1* | 4/2010 | Balaban | G06N 7/08 706/14 |
| 2014/0135598 | A1* | 5/2014 | Weidl | A61B 5/48 600/300 |
| 2014/0309806 | A1* | 10/2014 | Ricci | G06F 21/31 701/1 |
| 2015/0066284 | A1* | 3/2015 | Yopp | B60K 28/06 701/29.2 |
| 2015/0149023 | A1* | 5/2015 | Attard | B60W 30/182 701/28 |
| 2016/0071418 | A1* | 3/2016 | Oshida | B60W 30/165 701/23 |
| 2016/0140299 | A1* | 5/2016 | Al Harbi | G16Z 99/00 705/2 |
| 2016/0297359 | A1* | 10/2016 | Kirsch | B60Q 1/52 |
| 2016/0303969 | A1* | 10/2016 | Akula | A61B 5/6893 |
| 2017/0101054 | A1* | 4/2017 | Dusane | G08G 1/096741 |
| 2017/0105104 | A1* | 4/2017 | Ulmansky | H04W 4/42 |
| 2017/0108342 | A1* | 4/2017 | Foreman | G01C 21/3691 |
| 2017/0151959 | A1* | 6/2017 | Boesen | B60W 50/12 |
| 2017/0219362 | A1* | 8/2017 | Bryson | G06Q 10/06311 |
| 2017/0364069 | A1* | 12/2017 | Colella | G08G 1/096783 |
| 2017/0370732 | A1* | 12/2017 | Bender | G08G 1/096838 |
| 2018/0120837 | A1* | 5/2018 | Regmi | A61B 5/11 |
| 2018/0308064 | A1* | 10/2018 | Glaser | G01C 21/3423 |
| 2018/0338241 | A1* | 11/2018 | Li | H04W 4/40 |
| 2018/0375939 | A1* | 12/2018 | Magalhães de Matos | H04L 41/12 |
| 2018/0376305 | A1* | 12/2018 | Ramalho de Oliveira | H04W 4/44 |
| 2018/0376306 | A1* | 12/2018 | Ramalho de Oliveira | G08G 1/0112 |
| 2019/0041854 | A1* | 2/2019 | Millhouse | G16H 10/60 |
| 2019/0359056 | A1* | 11/2019 | Wilson | B60N 2/0024 |
| 2019/0359355 | A1* | 11/2019 | Wilson | A61B 5/18 |
| 2019/0361437 | A1* | 11/2019 | Wilson | G06F 40/58 |
| 2019/0361451 | A1* | 11/2019 | Wilson | G06Q 10/047 |
| 2020/0062172 | A1* | 2/2020 | Lujan | B60W 30/16 |
| 2020/0142407 | A1* | 5/2020 | Kozloski | G01C 21/3484 |
| 2020/0150667 | A1* | 5/2020 | Rakshit | G01C 21/30 |
| 2020/0245141 | A1* | 7/2020 | Antonatos | G06Q 50/40 |
| 2021/0078490 | A1* | 3/2021 | Lujan | B60Q 5/00 |
| 2022/0005140 | A1* | 1/2022 | Beaurepaire | G06F 16/9535 |
| 2022/0359064 | A1* | 11/2022 | Pierson | G16H 40/40 |
| 2023/0064950 | A1* | 3/2023 | Engle | G05D 1/69 |

OTHER PUBLICATIONS

Doctr, Doctr—ER wait times in Canad, retrieved from internet, retrieved on Sep. 30, 2022, <URL: https://play.google.com/store/apps/details?id=ca.doctr&hl=en_CA&gl=US>.

Joseph Guarisco, et al., Real Time Emergency Department Patient Wait Times on the Web, retrieved from internet, retrieved on Sep. 30, 2022, <URL: https://www.iise.org/SHS/Details.aspx?id=24152>.

Ergent, LLC, ERgent—Emergency Room Wait Time App, retrieved from internet, retrieved on Nov. 2, 2020, <URL: https://play.google.com/store/apps/details?id=com.ergent>.

Don Mitchell, Hamilton hospitals post real-time emergency room wait times online, retrieved on Sep. 30, 2022, <URL: https://globalnews.ca/news/6387106/hamilton-wait-times-online/>.

\* cited by examiner

METHOD AND SYSTEM TO FACILITATE PROVISIONING OF AN EMERGENCY HEALTH SERVICE

FIELD OF THE INVENTION

The present invention relates generally to a field of data processing. More specifically, the present invention includes methods and systems to facilitate provisioning of an emergency health service.

BACKGROUND OF THE INVENTION

According to a National Health Interview Survey (NHIS) conducted by National Centre for Health Statistics (NCHS), approximately there was 136.9 million emergency department (ED) visits every year in the United States, with only 35.4% of patients being seen in less than 15 minutes. As per the survey, the NCHS estimated ED use in the past year and the reasons for most ED visits. There were mutually exclusive categories including the seriousness of the medical problem, doctors' office or clinic was not open, and no access to care. Currently, 18-23% of the people use emergency rooms as primary care. Results in 2014 concluded that 18% of the adults visited the ED one or more times for medical problems, out of which 77% of adults were between 18-64. 12% of the adults visited ED because their doctor's office was not open, and 7% due to lack of access to other providers. The remaining 4% represent those in the survey who did not respond to the questions. These percentages were similar in 2013 and 2014 as well as in 2017. The survey consisted of adults with a variety of demographic differences and insurance carriers. Adults with Medicaid (a federal and state program of the United States that helps with medical costs for some people with limited income and resources) use the emergency department because of the severity of their medical problem. Adults with private insurance use the emergency department when their doctor's office and local clinics were closed, and uninsured adults due to the lack of accessibility to medical care. Minor changes in the emergency department use were noted between 2013 and 2014 and are factors in 2018. Also, walkouts cost emergency rooms $1.8 million each year in revenue. Currently, in Yale New Haven Hospital, the total average waiting period is 232 minutes. This figure is significant for overcrowding to occur in the ED. A study of almost a million admissions to 187 hospitals in California found that patients who were admitted after going through a very crowded emergency room were at 5 percent greater odds of dying than those admitted after passing through a less-crowded emergency room. This overcrowding might be the reason for the spreading of infections amongst people, which eventually becomes dangerous in recent times owing to the pandemic, such as the novel Coronavirus-2019 (COVID-19).

In the United States, the emergency department industry presently makes $100,000 in sales. In 2018, it has been observed that urgent care providers are taking marketing seriously and using data for direction. Many on-demand healthcare providers are partnering with trusted agencies or adding dedicated marketing staff to ensure they reach their marketing goals and engage with their patients. Because technology has such a big impact on how we market, clinics choosing to grow their marketing in-house should identify their level of expertise before determining strategy and be sure they have the know-how to develop and deliver on-target marketing. Without a thorough understanding of marketing complexities, the wrong choices can have a long-term impact on the clinic. As seen, many urgent care organizations are currently partnering with agencies to get the most return on their marketing investments. When considering an agency, they're looking for marketing experts that also have a finger on the pulse of the healthcare ecosystem. Finding a marketing partner with a slate of experts that understand business and objectives should pay out with more patients and financial benefits. As healthcare technology companies become more sophisticated, they gain access to relevant data that can help inform marketing initiatives. Some of these tech companies, understanding the importance of data, are offering marketing services to their customers. These services can be as simple as offering Google Analytics to measure digital advertising-return on investment (ROI) or track social networking sites and applications. At the other end of the spectrum, others are offering a broader range of marketing products as a partner, committed to the success of their customers. As marketing becomes more important across healthcare, brand management is increasingly on the radar of urgent care providers. Clinics are defining and redefining who they are, and who they want to be based on their strengths and the demographics of the patients they want based realistically on location, and strategically planning how to reach them. Further, the patient-centric market means creating a digital strategy including SEM (Search Engine Marketing) with sophisticated keyword bidding and SEO-rich (Search Engine Optimization) content on the website. Beyond the brand, consumers are looking for real value and helpful information. They don't want to be sold but are wanting to be informed. That means urgent care providers must create and deliver smarter content that appeals to patients. So along with promotional messaging, urgent care providers must deliver educational content via blog posts, contributed articles, video, and social messages that will help patients manage their health and healthcare decisions. Community-based marketing has also been a big part of the equation in 2018. Clinics are reaching into their communities and participating in health fairs and events that grow brand awareness and build their reputation. They are becoming sponsors for local sports teams and donating to important causes that affect the lives of people in their neighbourhoods. For urgent care providers, a common marketing challenge is attribution; figuring out what is working, is one of the primary benefits of partnering with professional marketers who understand the business.

Research shows that consumers in the emergency department industry primarily focus on factors such as the annual volume of incoming patients, which is estimated to be around 100,000 patients; assumed current average professional fee reimbursement, which is $125 per patient visit; leave without treatment (LWOT) annual rate, which is 3% and loss in professional fee revenue corresponding to impact of the LWOT is estimated to be $375,000; chart leakage, which is 1% and loss corresponding to the chart leakage is estimated to be $125,000. This impact of LWOT and the chart leakage amounts to $500,000 in professional fee revenue.

Few organizations utilize emergency management services, in which major hospitals currently offer timeframes and wait statuses but the facility is solely for the concerned organization. The organizations also offer virtual access to triage services along with vitals but the service is not approved for Medicaid-insured patients. Some of the hospitals such as John Hopkins Hospital offers emergency services with check-ins and time managed visits, Saint Vincent's Ascension program offers managed emergency room visit through virtual check-ins and timeframes and wait statuses but only serviced through the concerned organization, and United Concierge Medicine offers virtual access to emergency services, treatment, triage, and analytics. Further, the concerned organizations do not offer services to patients with Medicaid insurance, which is a drawback.

Existing techniques to facilitate provisioning of an emergency health service are deficient with regard to several aspects. For instance, current technologies do not provide convenient means to patients for accessing emergency room services of emergency rooms in emergency departments of healthcare facilities, which becomes the utmost reason for overcrowding in the emergency departments. Further, current technologies do not provide affordable means to the patients for accessing the emergency room services of the emergency rooms considering socio-economic statuses of the patients. Furthermore, current technologies do not provide transportation facilities to the patient for transporting the patients to the healthcare facilities. Moreover, current technologies do not provide the patients with 24-hours access to live service providers such as registered nurses, licensed clinical social workers, and patient advocates.

Therefore, there is a need for improved methods and systems to facilitate provisioning of an emergency health service that may overcome one or more of the above-mentioned problems and/or limitations.

DETAIL DESCRIPTIONS OF THE INVENTION

All illustrations of the drawings are for the purpose of describing selected versions of the present invention and are not intended to limit the scope of the present invention.

Figure 1:
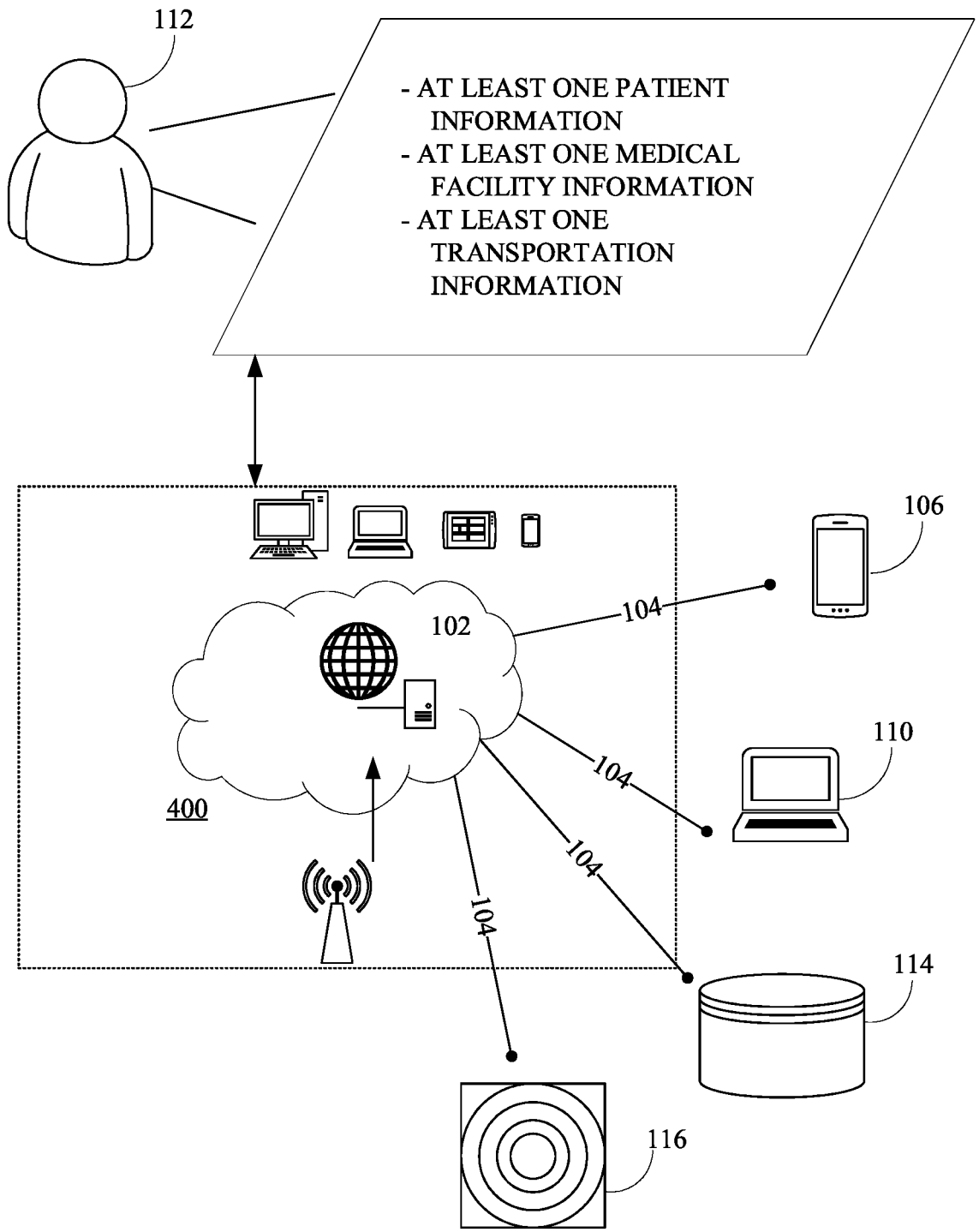
FIG. 1 is an illustration of an online platform consistent with various embodiments of the present disclosure.

FIG. 1 is an illustration of an online platform 100 consistent with various embodiments of the present disclosure. By way of non-limiting example, the online platform 100 to enable facilitating management of driver location data and relevant data may be hosted on a centralized server 102, such as, for example, a cloud computing service. The driver location data and relevant data may include but are not limited to GPS location, timestamps of the driver on a test route, direction of travel of the driver, license plate of the driver, the toll road transponder associated with the driver, classification and number of axles of the automotive vehicle associated with the driver, signals captured from the toll transponder, software executions generated by the automotive vehicle associated with the driver and database records generated by an automotive vehicle associated with the driver. The centralized server 102 may communicate with other network entities, such as, for example, a mobile device 106 (such as a smartphone, a laptop, a tablet computer, in-vehicle infotainment system, a standalone hardware unit, etc.), other electronic devices 110 (such as desktop computers, server computers etc.), databases 114, and sensors 116 over a communication network 104, such as, but not limited to, the Internet. Further, users of the online platform 100 may include relevant parties such as, but not limited to, end-users, administrators, service providers, service consumers and so on. Accordingly, in some instances, electronic devices operated by the one or more relevant parties may be in communication with the platform.

A user 112, such as the one or more relevant parties, may access online platform 100 through a web-based software application or browser. The web-based software application may be embodied as, for example, but not be limited to, a website, a web application, a desktop application, and a mobile application compatible with a computing device 200.

Figure 2:
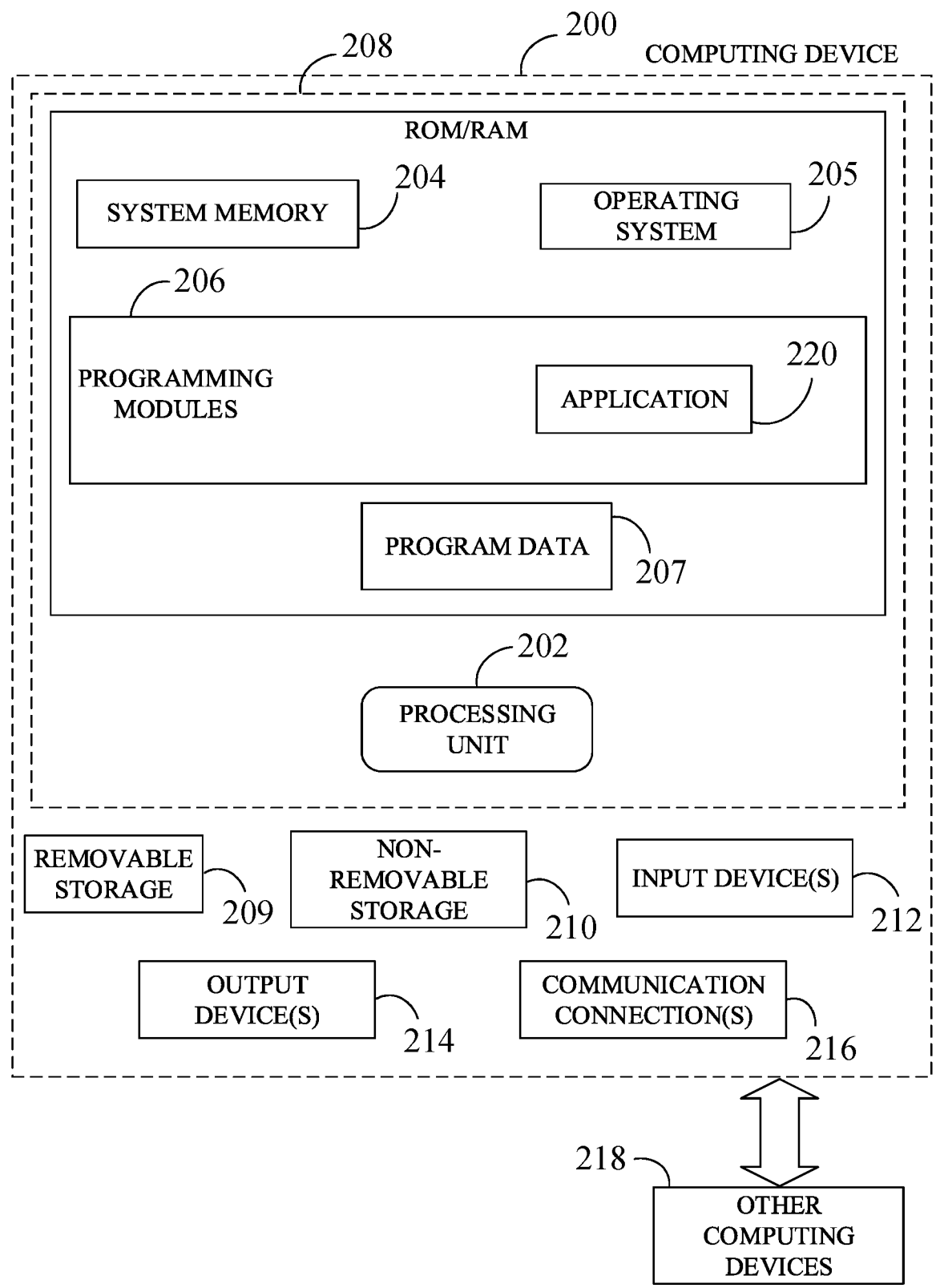
FIG. 2 is a block diagram of a computing device for implementing the methods disclosed herein, in accordance with some embodiments.

With reference to FIG. 2, a system consistent with an embodiment of the disclosure may include a computing device or cloud service, such as computing device 200. In a basic configuration, computing device 200 may include at least one processing unit 202 and a system memory 204. Depending on the configuration and type of computing device, system memory 204 may comprise, but is not limited to, volatile (e.g. random-access memory (RAM)), non-volatile (e.g. read-only memory (ROM)), flash memory, or any combination. System memory 204 may include operating system 205, one or more programming modules 206, and may include a program data 207. Operating system 205, for example, may be suitable for controlling computing device 200's operation. In one embodiment, programming modules 206 may include image-processing module, artificial intelligence and machine learning module. Furthermore, embodiments of the disclosure may be practiced in conjunction with a graphics library, other operating systems, or any other application program and is not limited to any particular application or system. This basic configuration is illustrated in FIG. 2 by those components within a dashed line 208.

Computing device 200 may have additional features or functionality. For example, computing device 200 may also include additional data storage mediums (removable and/or non-removable) such as, for example, magnetic disks, optical disks, or tape. Such additional storage is illustrated in FIG. 2 by a removable storage 209 and a non-removable storage 210. Computer storage media may include volatile and non-volatile, removable and non-removable media implemented in any method or technology for storage of information, such as computer-readable instructions, data structures, program modules, or other data. System memory 204, removable storage 209, and non-removable storage 210 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 200. Any such computer storage media may be part of device 200. Computing device 200 may also have input device(s) 212 such as a keyboard, a mouse, a pen, a sound input device, a touch input device, a location sensor, a camera, a biometric sensor, etc. Output device(s) 214 such as a display, speakers, a printer, etc. may also be included. The aforementioned devices are examples and others may be used.

Computing device 200 may also contain a communication connection 216 that may allow device 200 to communicate with other computing devices 218, such as over a network in a distributed computing environment, for example, an intranet or the Internet. Communication connection 216 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 204, including operating system 205. While executing on processing unit 202, programming modules 206 (e.g., application 220 such as a media player) may perform processes including, for example, one or more stages of methods, algorithms, systems, applications, servers, databases as described above. The aforementioned process is an example, and processing unit 202 may perform other processes. Other programming modules that may be used in accordance with embodiments of the present disclosure may include machine learning and artificial intelligence applications.

As can be seen in FIG. 1 through FIG. 11, the preferred embodiment of the present invention is a method and system to facilitate provisioning of an emergency health service. Further, the disclosed methods and systems aim to provide a patient with time frames and wait statuses before visiting an emergency room of an emergency department of any medical facility 4 in nearby areas, as the patient may be able to select a medical facility 4 from various medical facilities 4 based on a choice of the patient. Further, the present disclosure describes a method of inputting identifying information of the patient like name, date of birth, address, etc. along with the medical facility 4 of the choice as well as symptoms. The symptoms may then be temporarily stored in an emergency health service database, and subsequently, after that the patient chooses to share the symptoms with the medical facility 4, information is transferred from the emergency health service database and shared with the concerned medical facility 4. Further, the present disclosure describes a method of displaying the information using a dashboard, which makes the information accessible to the medical facility 4, making the provisioning of the emergency health service a two-sided service. Based on the information, medical facility 4 staff can determine wait status and timeframe for the patient requiring medical assistance and update them on an application downloaded on a device associated with the patient, leaving the patient in requirement of the medical assistance with two options, either to wait comfortably at home or arrange for a ride, thus enabling the patient to leave for the medical facility 4 in order to get medical assistance at the convenience of the patient at the right time. Further, the disclosed systems and methods aim to provide assistance to the patient by making emergency medical transportation (E.M.T) services and other transportation services like Uber and Lyft accessible at a time of urgency through a vouchered system specifically designed for transportation of the patient from a current location of the patient to the medical facility 4, and vice versa. Further, the disclosed systems and the methods aim to provide real-time assistance to the patient, enabling the patient to speak to a medical facility member such as a nurse using a nurses' hotline or for special cases, such as a suicide prevention hotline. Further, the present disclosure describes a method of reaching out to medical practitioners such as registered nurses, licensed clinicians, social workers, and patient advocates such that the patient may take vital actions at the time of urgency as advised by the medical practitioner before getting medical assistance. The dashboard ensures that the medical assistance is given based on a triage upon identifying the patient reaching the medical facility 4. Further, the disclosed systems and methods aim to expand the emergency healthcare service by providing emergency health service kiosks 13 in near future, which can include kiosks 13 strategically placed around the cities for homeless people and people who may not have Wi-Fi or internet access to access emergency health services.

Figure 3:
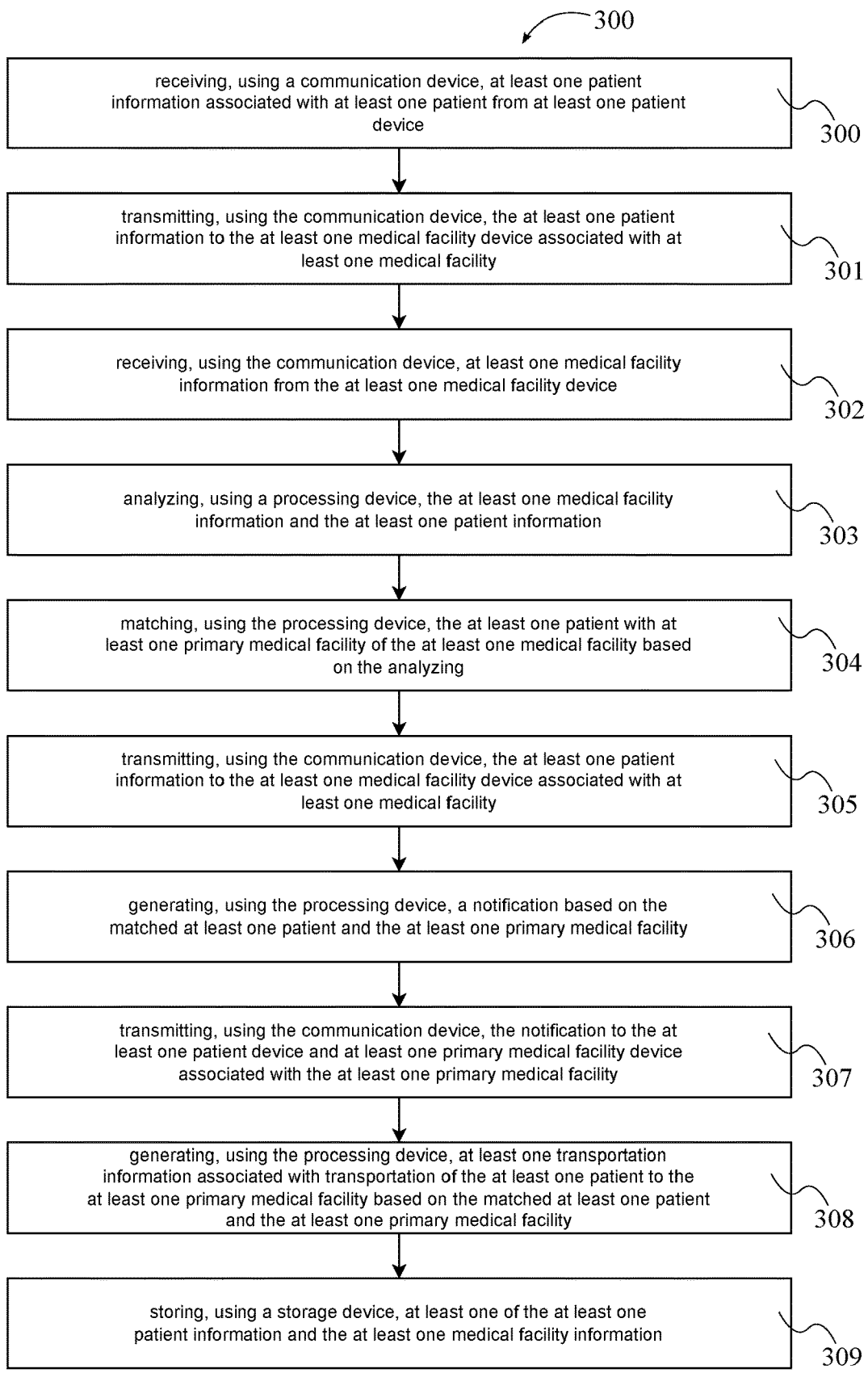
FIG. 3 is an illustration of a flowchart of the present invention.

As can be seen in FIG. 3, the system 1100 used to execute the method 300 of the present invention allows the present invention to connect patients with nearby health care providers. To accomplish this, the method of the present invention may include a step 301 of receiving, using a communication device 1, at least one patient information associated with at least one patient from at least one patient device 12. The communication device 1 is an electronic device capable of sending and receiving information to external devices such as a client device, third party device, public database, etc. The patient information is the contact information such as name, address, phone number and email that relates to the patient. As a result, the patient provides important patient information associated with the patient. The system 1100 used to execute the method of the present invention may include a step 302 of transmitting, using the communication device 1, the at least one patient information to the at least one medical facility device 11 associated with at least one medical facility 4. The medical facility 4 is a facility capable of providing health care to a variety of different patients such as a hospital, urgent care, doctors office, etc. Consequently, the patient information will be sent to a medical facility 4 to ensure the proper care can be provided to the patient. The system 1100 used to execute the method of the present invention may include a step 303 of receiving, using the communication device 1, at least one medical facility information from the at least one medical facility device 11. Accordingly, the medical facility 4 has all the necessary information required about a patient. For example, a patient could utilize their own mobile device with a mobile application to fill out their personal information on a dashboard pertaining to their medical history and contact information that is then sent to various medical facilities within the area.

As can be seen in FIG. 3, the system 1100 used to execute the method 300 of the present invention allows the present invention to match patients with the appropriate health care provider. To accomplish this, the method of the present invention may include a step 304 of analyzing, using a processing device 2, the at least one medical facility information and the at least one patient information. Thus, the patient can be properly analyzed for the patient's needs. The system 1100 used to execute the method of the present invention may include a step 305 of matching, using the processing device 2, the at least one patient with at least one primary medical facility 41 of the at least one medical facility 4 based on the analyzing. So, the patient is matched with a primary medical facility 41 that is both close by and will meet the needs of the patient. The system 1100 used to execute the method of the present invention may include a step 306 of generating, using the processing device 2, a notification based on the matched at least one patient and the at least one primary medical facility 41. As a result, the processing device 2 creates a notification that shows up on the communication device 1 that the patient is utilizing. For example, once a patient is matched up with a proper primary medical facility 41 within the area a notification could be sent to their mobile device providing them with the proper information needed.

As can be seen in FIG. 3, the system 1100 used to execute the method 300 of the present invention allows the present invention to provide the patient with transportation and wait time information for the primary medical facility 41 selected. To accomplish this, the method of the present invention may include a step 307 of transmitting, using the communication device 1, the notification to the at least one patient device 12 and at least one primary medical facility 41 device 111 associated with the at least one primary medical facility 41. The medical facility device 11 is a device configured to display a dashboard associated with the provisioning of the emergency health service. Further, the dashboard, in an instance, may display the at least one patient information based on the transmitting. Further, the dashboard, in an instance, may display names of one or more of the at least one patient, a sequence list associated with the one or more of the at least one patient, symptoms of the one or more of the at least one patient, etc. Further, the at least one medical facility device 11 may include a device such as, but are not limited to, a smartphone, a laptop, a PC, and so on. The system 1100 used to execute the method of the present invention may include a step 308 of generating, using the processing device 2, at least one transportation information associated with transportation of the at least one patient to the at least one primary medical facility 41 based on the matched at least one patient and the at least one primary medical facility 41. The transportation information may include at least one route. Further, the transportation, in an instance, may be provided by the at least one transporter. Further, the generating of the at least one transportation information may be based on the at least one status of the at least one medical care (such as, the wait status, the timeframe, etc.). Further, the at least one transporter, in an instance, may include at least one emergency medical transportation (EMT) service provider, at least one transportation service provider, etc. Further, the at least one EMT service provider may provide at least one EMT service for the transportation of the at least one patient to the at least one primary medical facility 41. Further, the at least one EMT service may include an ambulance service. Further, the at least one transportation service provider may provide at least one transportation service for the transportation of the at least one patient to the at least one primary medical facility 41. Further, the at least one transportation service, in an instance, may include Uber, Lyft, etc. Further, the at least one route may be a path that may be traversed by the at least one transporter to facilitate the transporting of the at least one patient from the location of the at least one patient to the at least one primary medical facility 41. The system 1100 used to execute the method of the present invention may include a step 309 of storing, using a storage device 3, at least one of the at least one patient information and the at least one medical facility information. The storage device 3 provides a reliable storage of digital information for data storage or data retrieval operations.

Figure 4:
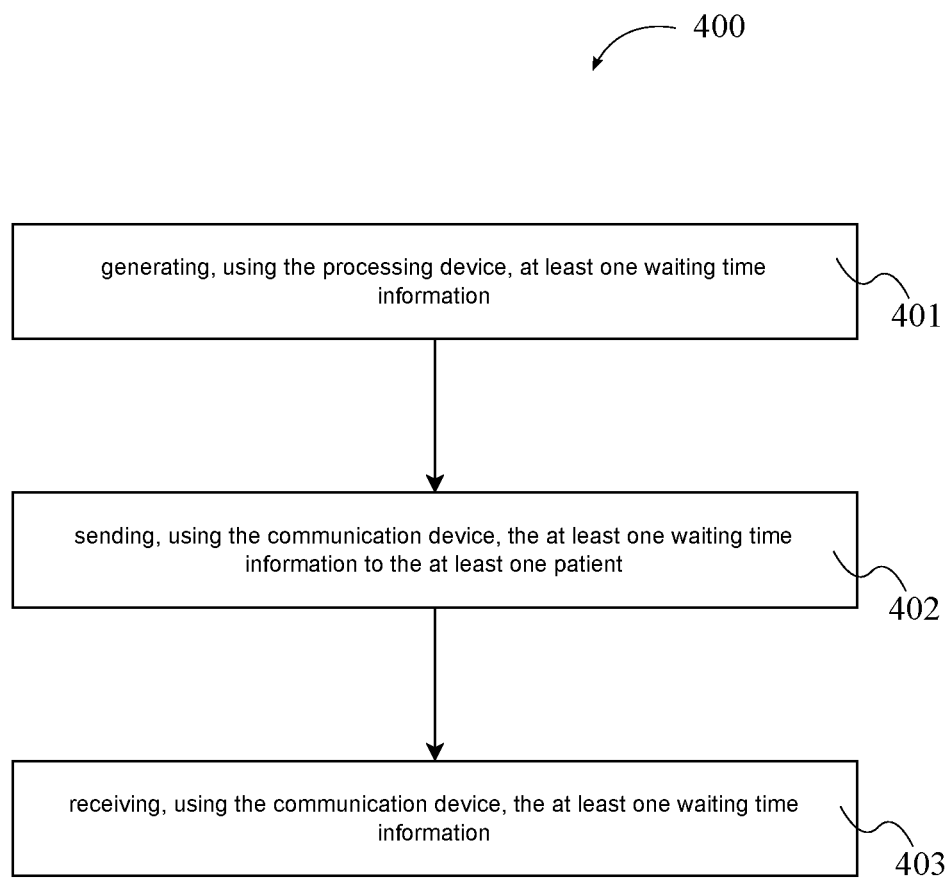
FIG. 4 is an illustration of a flowchart of the present invention.

In reference to FIG. 4, a sub-process 400 of the method 300 of the present invention provides patients with an estimated wait time for their appointment at a medical facility 4. To that end, the sub-process 400 begins with a step 401 of generating, using the processing device 2, at least one waiting time information. The waiting time information is displayed on the dashboard that is updated in real time showing the amount of time the patient must wait for their appointment. The sub-process 400 continues with a step 402 of sending, using the communication device 1, the at least one waiting time information to the at least one patient. The sub-process 400 continues with a step 403 of receiving, using the communication device 1, the at least one waiting time information. For example, once a patient is paired up with a primary medical facility 41 a real time updating notification is sent to the patient showing the wait time before the patient will be seen by a medical professional at the primary medical facility 41.

Figure 5:
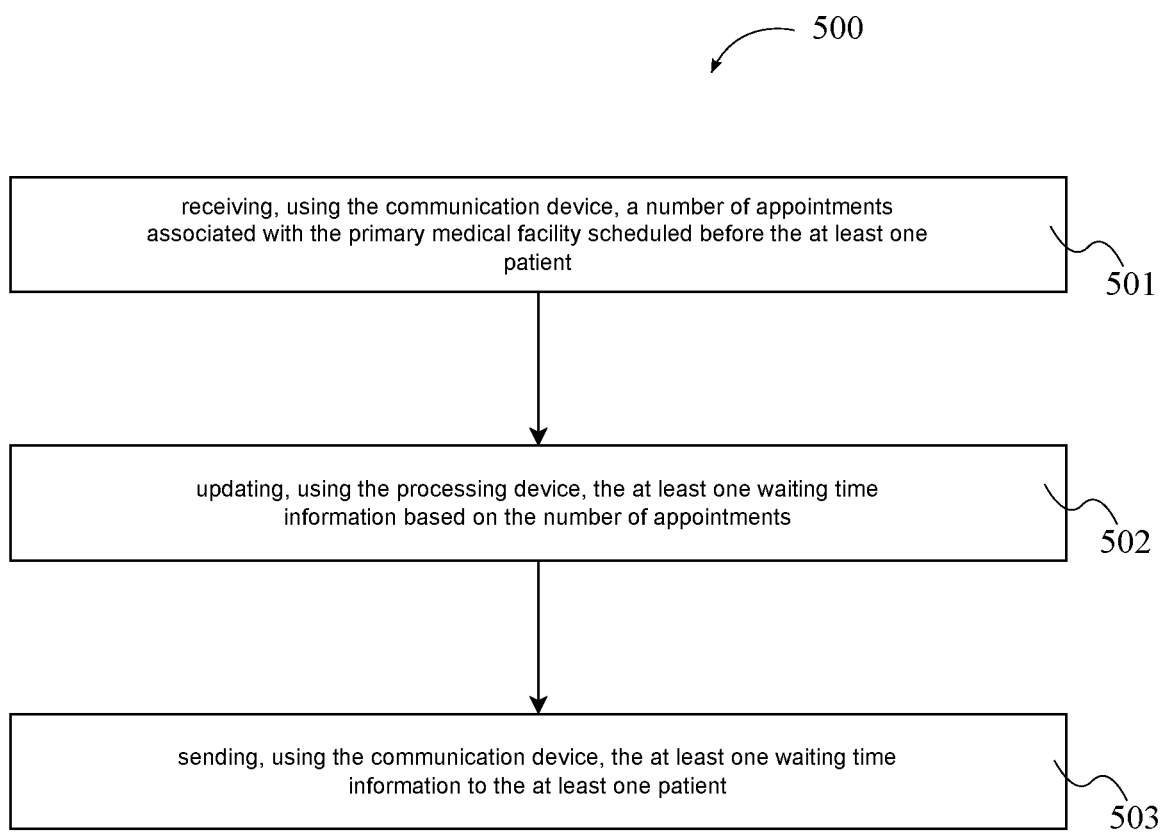
FIG. 5 is an illustration of a flowchart of the present invention.

In reference to FIG. 5, a sub-process 500 of the method 300 of the present invention enables provide patients with an updated wait time. To that end, the sub-process 500 begins with a step 501 of receiving, using the communication device 1, a number of appointments associated with the primary medical facility 41 scheduled before the at least one patient. This provides the communication device 1 with the number of other patients that need to be seen before the patient utilizing the present invention can be seen. The sub-process 500 continues with a step 502 of updating, using the processing device 2, the at least one waiting time information based on the number of appointments. As the number of other patients are seen by the medical facility 4 the number of patients in line will decrease, affecting the wait time for the patient utilizing the present invention. The sub-process 500 continues with a step 503 of sending, using the communication device 1, the at least one waiting time information to the at least one patient. For example, as other patients are seen by the medical facility 4 the processing device 2 will re-calculate a new wait time for the patient and send an updated wait time to the communication device 1 that the patient is using.

Figure 6:
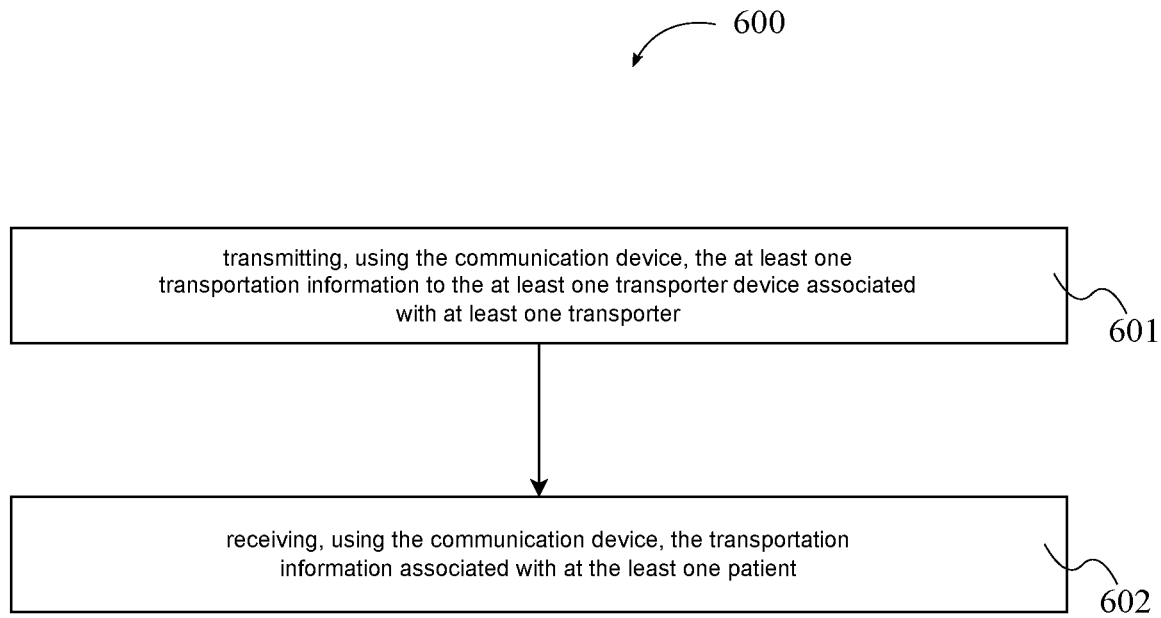
FIG. 6 is an illustration of a flowchart of the present invention.

In reference to FIG. 6, a sub-process 600 of the method 300 of the present invention provides a transporter with instructions on how to reach the primary medical facility 4. To that end, the sub-process 600 begins with a step 601 of transmitting, using the communication device 1, the at least one transportation information to the at least one transporter device associated with at least one transporter. As a result, the transporter is provided the location of the primary medical facility 41 to allow a transporter the option to complete a nearby trip. The sub-process 600 continues with a step 602 of receiving, using the communication device 1, the transportation information associated with at the least one patient. the transporter is provided the location of the patient and the primary medical facility 41 to ensure a complete trip between the two destinations.

Figure 7:
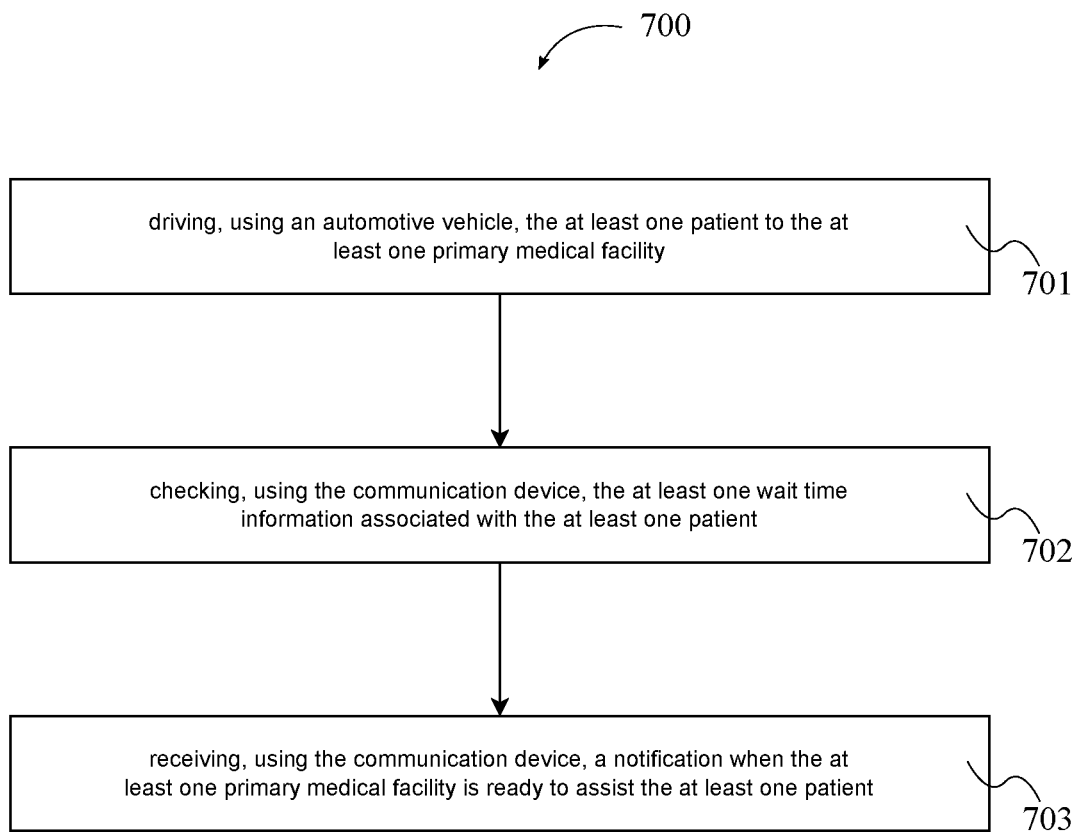
FIG. 7 is an illustration of a flowchart of the present invention.

In reference to FIG. 7, a sub-process 700 of the method 300 of the present invention enables the patient to travel to the primary medical facility 41. To that end, the sub-process 700 begins with a step 701 of driving, using an automotive vehicle, the at least one patient to the at least one primary medical facility 41. Consequently, the patient is transported to the primary medical facility 41. The sub-process 700 continues with a step 702 of checking, using the communication device 1, the at least one wait time information associated with the at least one patient. Accordingly, the patient can check the amount of time left before they can enter the primary medical facility 41 and be seen by a medical professional. The sub-process 700 continues with a step 703 of receiving, using the communication device 1, a notification when the at least one primary medical facility 41 is ready to assist the at least one patient. Thus, the patient is notified when they are ready to be seen by a medical professional. For example, as the patient reaches the medical facility 4 they can safely wait within their vehicle instead of going into a waiting room and can then be sent a notification when they are ready to be seen by the primary medical facility 41.

Figure 8:
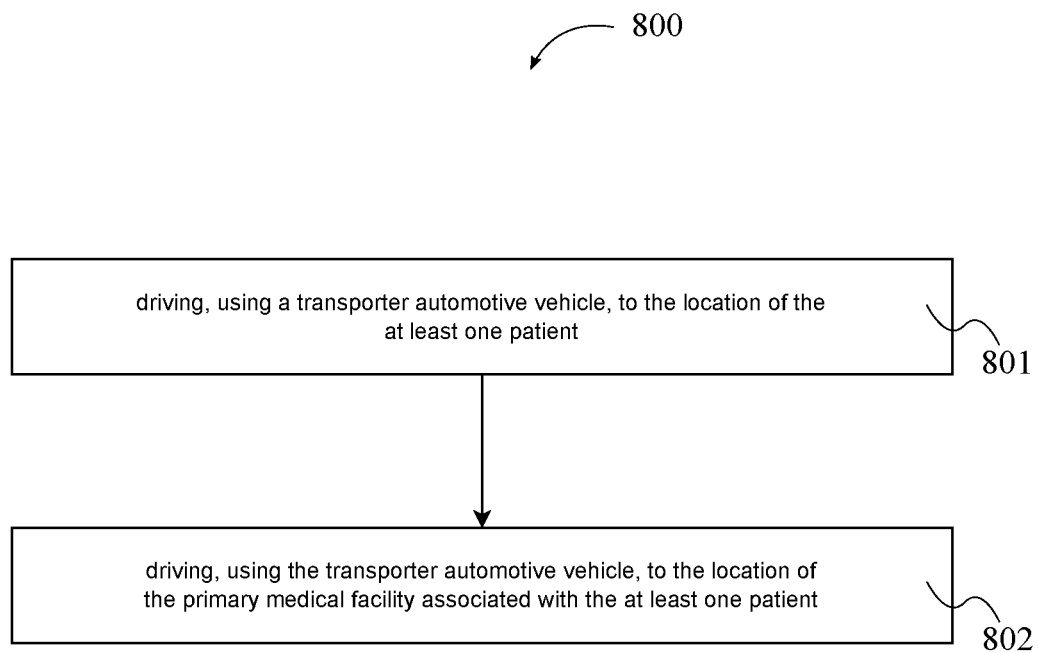
FIG. 8 is an illustration of a flowchart of the present invention.

In reference to FIG. 8, a sub-process 800 of the method 803 of the present invention provides the patient a way to get to the primary medical facility 41 without having their own automotive vehicle. To that end, the sub-process 800 begins with a step 801 of driving, using a transporter automotive vehicle, to the location of the at least one patient. The transporter automotive vehicle will provide the patient a method of transportation to the primary medical facility 41. The transporter automotive vehicle could be any $3^{rd}$ party service such as an ambulance, Uber, Lyft, or carsharing platform. The sub-process 800 continues with a step 802 of driving, using the transporter automotive vehicle, to the location of the primary medical facility 41 associated with the at least one patient.

Figure 9:
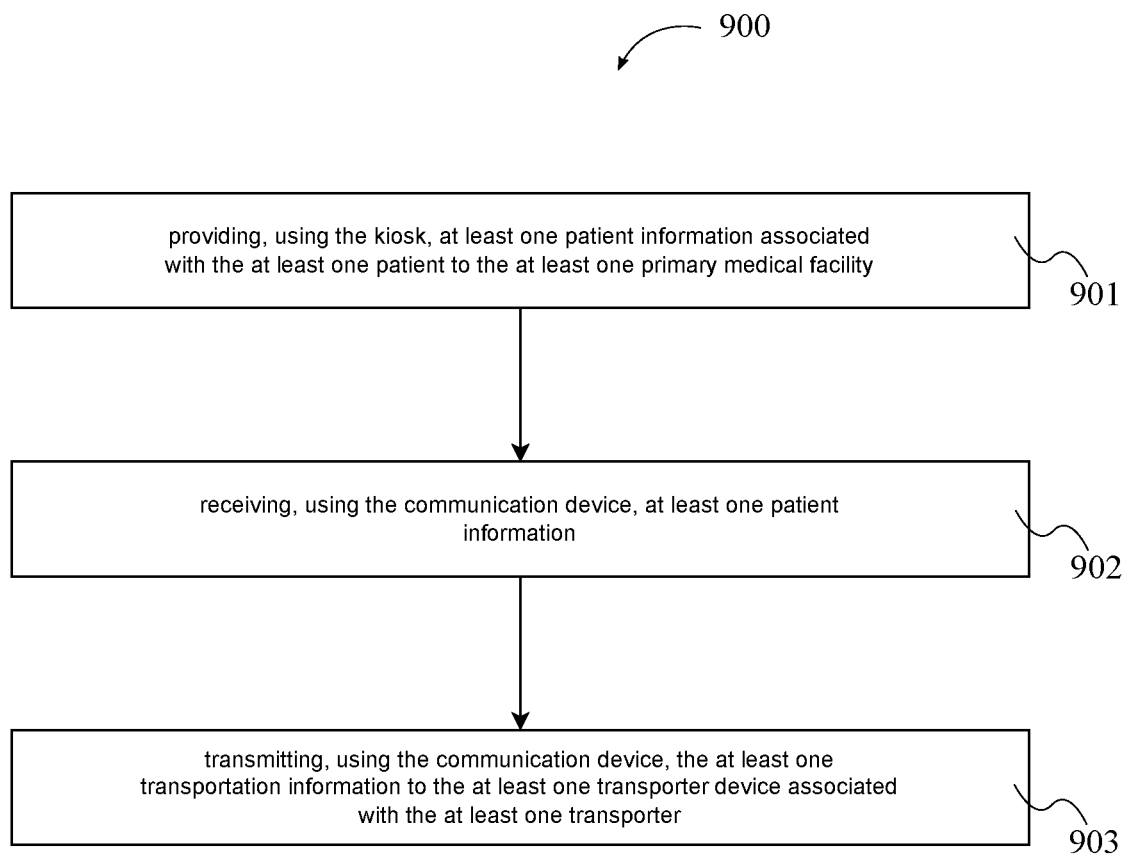
FIG. 9 is an illustration of a flowchart of the present invention.

In reference to FIG. 9, a sub-process 900 of the method 300 of the present invention enables patients without convenient access to various mobile electronic devices to still communicate with a medical facility 4. To that end, the sub-process 900 begins with a step 901 of providing, using a kiosk 13, at least one patient information associated with the at least one patient to the at least one primary medical facility 41. So, the kiosk 13 will be positioned strategically around various low-income neighborhoods to allow for patients to easily connect with medical facilities. The sub-process 900 continues with a step 902 of receiving, using the communication device 1, at least one patient information. As a result, the patient is able to input their information into the kiosk 13 that is then sent by the communication device 1. The sub-process 900 continues with a step 903 of transmitting, using the communication device 1, the at least one transportation information to the at least one transporter device associated with the at least one transporter. Consequently, the communication device 1 provides the transporter with the location information the patient enters into the kiosk 13. For example, a patient can walk up to a kiosk 13 placed in a neighborhood and enter their personal information. The kiosk 13 will then connect them with a medical facility 4 and a transporter who till then transport them to the connected medical facility 4.

Figure 10:
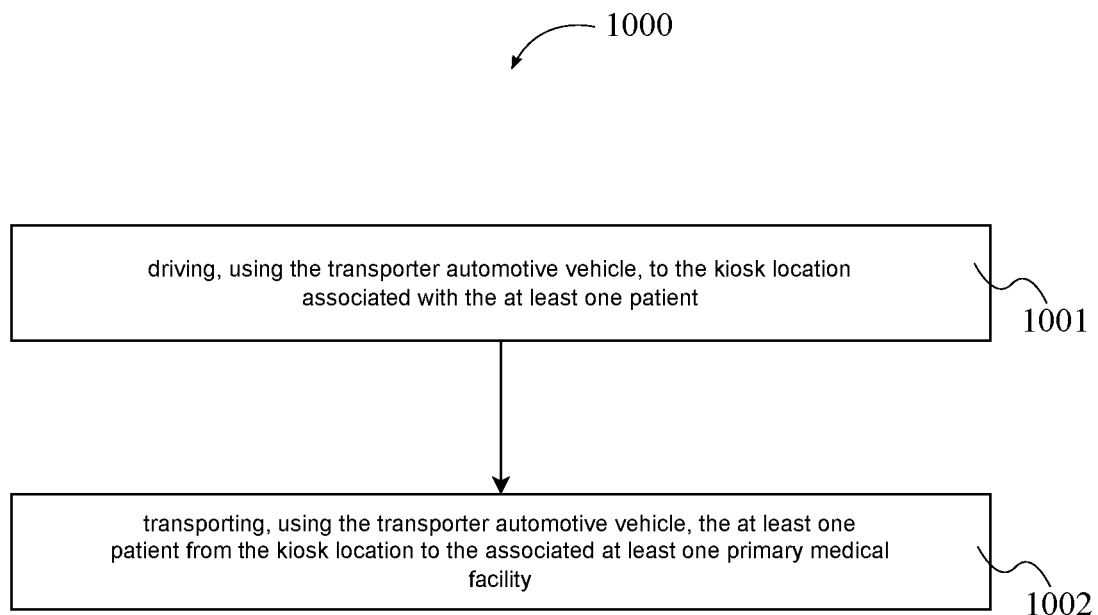
FIG. 10 is an illustration of a flowchart of the present invention.

In reference to FIG. 10, a sub-process 1000 of the method 300 of the present invention enables patients to be transported from the kiosk 13 to the primary medical facility 41. To that end, the sub-process 100 begins with a step 1001 of driving, using the transporter automotive vehicle, to the kiosk 13 location associated with the at least one patient. Accordingly, the transporter automotive vehicle will reach the location of the patient at the kiosk 13. The sub-process 1000 continues with a step 1002 of transporting, using the transporter automotive vehicle, the at least one patient from the kiosk 13 location to the associated at least one primary medical facility 41. Thus, the patient is then transported to the medical facility 4 from the kiosk 13 in a way that does not create a large expense for the patient.

Figure 11:
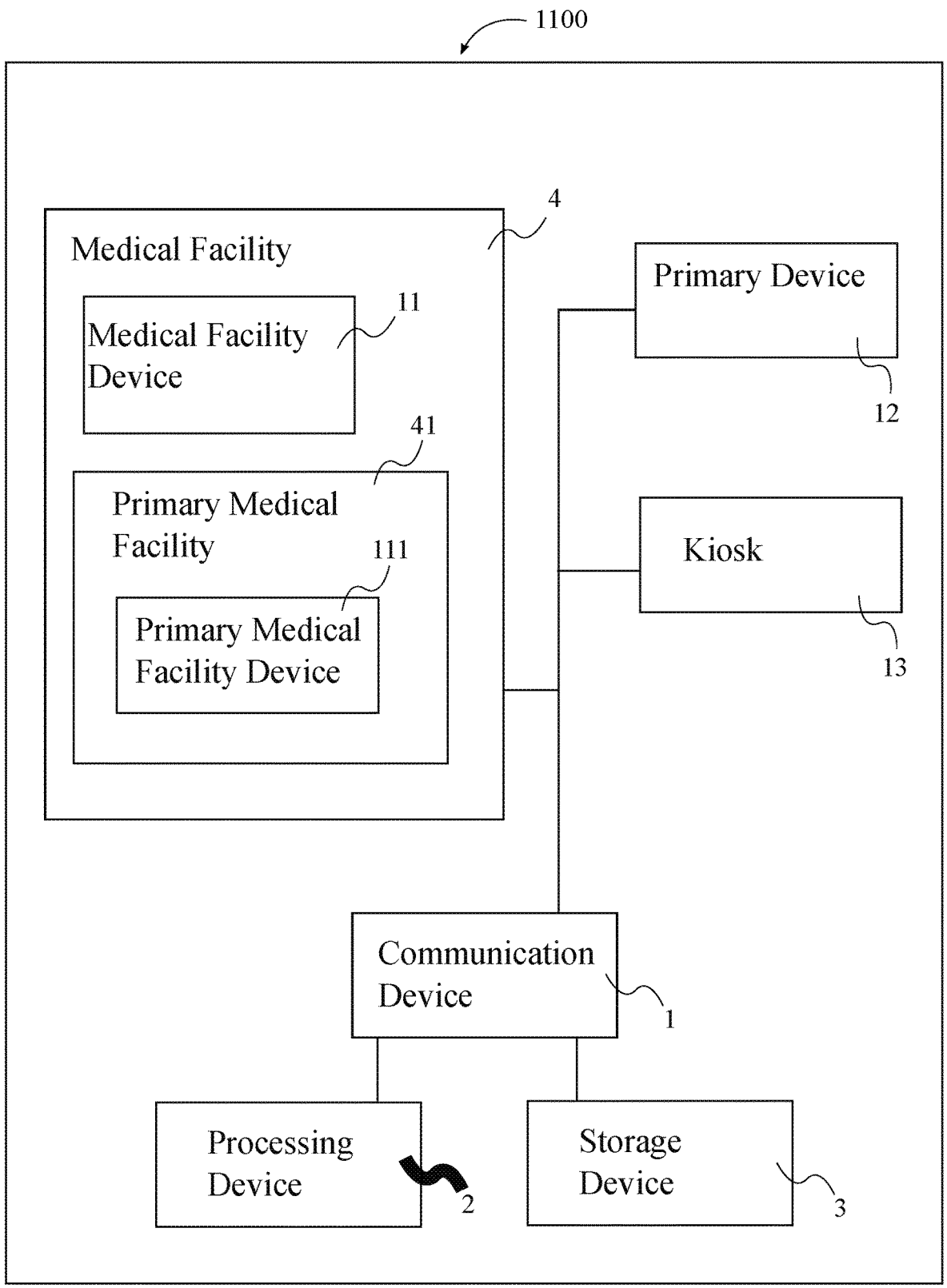
FIG. 11 is a block diagram of the system of the present invention.

FIG. 11, illustrates a block diagram of a system to facilitate provisioning of an emergency health service, in accordance with some embodiments. Accordingly, the system may include a communication device 1. Further the communication device 1 may be configured for receiving at least one patient information associated with at least one patient from at least one patient device 12. Further, the communication device 1 may be configured for transmitting the at least one patient information to the at least one medical facility device 11 associated with at least one medical facility 4. Further, the communication device 1 may be configured for receiving at least one medical facility information from the at least one medical facility device 11. Further, the communication device 1 may be configured for transmitting the notification to the at least one patient device 12 and at least one primary medical facility device 111 associated with the at least one primary medical facility 41. Further, the system may include a processing device 2 communicatively coupled to the communication device 1. Further the processing device 2 may be configured for analyzing the at least one medical facility information and the at least one patient information. Further, the processing device 2 may be configured for matching the at least one patient with at least one primary medical facility 41 of the at least one medical facility 4 based on the analyzing. Furthermore, the processing device 2 may be configured for generating a notification based on the matched at least one patient and the at least one primary medical facility 41. Further, the processing device 2 may be configured for generating at least one transportation information associated with transportation of the at least one patient to the at least one primary medical facility 41 based on the matched at least one patient and the at least one primary medical facility 41. Further, the system may include a storage device 3 further communicatively coupled to the processing device 2. Further, the storage device 3 may be configured for storing at least one of the at least one patient information and the at least one medical facility information.

Further, the system 1100 may include a processing device 2 further configured for generating at least one waiting time information. Further, the system may include a communication device 1 further configured for sending the at least one waiting time information to the at least one patient. Further, the communication device 1 may be configured for receiving the at least one waiting time information.

Further, the system 1100 may include the communication device 1 further configured for receiving a number of appointments associated with the primary medical facility 41 scheduled before the at least one patient. Further, the communication device 1 may be configured for sending the at least one waiting time information to the at least one patient. Further, the system may include the processing device 2 further configured for updating the at least one waiting time information based on the number of appointments. Further, the communication device 1 further configured for transmitting the at least one transportation information to the at least one transporter device associated with at least one transporter. Further, the communication device 1 further configured for receiving the transportation information associated with at the least one patient.

Further, the system 1100 may include an automotive vehicle communicatively coupled with the processing device 2. Further, the automotive vehicle may be configured for driving the at least one patient to the at least one primary medical facility 41. Further, the system may include the communication device 1 further configured for checking the at least one wait time information associated with the at least one patient. Further, the communication device 1 configured for receiving a notification when the at least one primary medical facility 41 is ready to assist the at least one patient. Furthermore, the system may include a transporter automotive vehicle communicatively coupled with the processing system. The transporter automotive vehicle may be configured for driving to the location of the at least one patient. Further, the transporter automotive vehicle may be configured for driving to the location of the primary medical facility 41 associated with the at least one patient.

Further, the system 1100 may include a kiosk 13 device communicatively coupled with the processing device 2. Further, the kiosk 13 device may be configured for providing at least one patient information associated with the at least one patient to the at least one primary medical facility 41. Further, the system may include the communication device 1 further configured for receiving at least one patient information. Further, the communication device 1 may be configured for transmitting the at least one transportation information to the at least one transporter device associated with the at least one transporter. Further the transporter automotive vehicle may be configured for driving to the kiosk 13 location associated with the at least one patient. Further, the transporter automotive vehicle may be configured for transporting the at least one patient from the kiosk 13 location to the associated at least one primary medical facility 41.

Although the invention has been explained in relation to its preferred embodiment, it is to be understood that many other possible modifications and variations can be made without departing from the spirit and scope of the invention as hereinafter claimed.

What is claimed is:

1. A method to facilitate provisioning of an emergency health service comprising:
   receiving, using a communication device, at least one patient information associated with at least one patient from at least one patient device;
   transmitting, using the communication device, the at least one patient information to the at least one medical facility device associated with at least one medical facility;
   receiving, using the communication device, at least one medical facility information from the at least one medical facility device;
   analyzing, using a processing device, the at least one medical facility information and the at least one patient information;
   matching, using the processing device, the at least one patient with at least one primary medical facility of the at least one medical facility based on the analyzing;
   generating, using the processing device, a notification based on the matched at least one patient and the at least one primary medical facility;
   transmitting, using the communication device, the notification to the at least one patient device and at least one primary medical facility device associated with the at least one primary medical facility;
   generating, using the processing device, at least one transportation information associated with transportation of the at least one patient to the at least one primary medical facility based on the matched at least one patient and the at least one primary medical facility;
   storing, using a storage device, at least one of the at least one patient information and the at least one medical facility information;
   generating, using the processing device, at least one waiting time information,
   sending, using the communication device, the at least one waiting time information to the at least one patient; and
   receiving, using the communication device, the at least one waiting time information.

2. The method to facilitate provisioning of an emergency health service as claimed in claim 1 comprising:
   receiving, using the communication device, a number of appointments associated with the primary medical facility scheduled before the at least one patient;
   updating, using the processing device, the at least one waiting time information based on the number of appointments; and
   sending, using the communication device, the at least one waiting time information to the at least one patient.

3. The method to facilitate provisioning of an emergency health service as claimed in claim 1 comprising:
   transmitting, using the communication device, the at least one transportation information to the at least one transporter device associated with at least one transporter; and
   receiving, using the communication device, the transportation information associated with at the least one patient.

4. The method to facilitate provisioning of an emergency health service as claimed in claim 3 comprising:
   driving, using an automotive vehicle, the at least one patient to the at least one primary medical facility;
   checking, using the communication device, the at least one wait time information associated with the at least one patient; and
   receiving, using the communication device, a notification when the at least one primary medical facility is ready to assist the at least one patient.

5. The method to facilitate provisioning of an emergency health service as claimed in claim 3 comprising:
   driving, using a transporter automotive vehicle, to the location of the at least one patient; and
   driving, using the transporter automotive vehicle, to the location of the primary medical facility associated with the at least one patient.

6. The method to facilitate provisioning of an emergency health service as claimed in claim 1 comprising:
   providing, using a kiosk, at least one patient information associated with the at least one patient to the at least one primary medical facility;
   receiving, using the communication device, at least one patient information; and
   transmitting, using the communication device, the at least one transportation information to the at least one transporter device associated with the at least one transporter.

7. The method to facilitate provisioning of an emergency health service as claimed in claim 6 comprising:
   driving, using the transporter automotive vehicle, to the kiosk location associated with the at least one patient; and
   transporting, using the transporter automotive vehicle, the at least one patient from the kiosk location to the associated at least one primary medical facility.

8. A method to facilitate provisioning of an emergency health service comprising:
   receiving, using a communication device, at least one patient information associated with at least one patient from at least one patient device;

transmitting, using the communication device, the at least one patient information to the at least one medical facility device associated with at least one medical facility;

receiving, using the communication device, at least one medical facility information from the at least one medical facility device;

analyzing, using a processing device, the at least one medical facility information and the at least one patient information;

matching, using the processing device, the at least one patient with at least one primary medical facility of the at least one medical facility based on the analyzing generating, using the processing device, a notification based on the matched at least one patient and the at least one primary medical facility;

transmitting, using the communication device, the notification to the at least one patient device and at least one primary medical facility device associated with the at least one primary medical facility;

generating, using the processing device, at least one transportation information associated with transportation of the at least one patient to the at least one primary medical facility based on the matched at least one patient and the at least one primary medical facility;

storing, using a storage device, at least one of the at least one patient information and the at least one medical facility information;

generating, using the processing device, at least one waiting time information;

sending, using the communication device, the at least one waiting time information to the at least one patient;

receiving, using the communication device, the at least one waiting time information;

receiving, using the communication device, a number of appointments associated with the primary medical facility scheduled before the at least one patient;

updating, using the processing device, the at least one waiting time information based on the number of appointments;

sending, using the communication device, the at least one waiting time information to the at least one patient;

transmitting, using the communication device, the at least one transportation information to the at least one transporter device associated with at least one transporter;

receiving, using the communication device, the transportation information associated with at the least one patient;

driving, using an automotive vehicle, the at least one patient to the at least one primary medical facility;

checking, using the communication device, the at least one wait time information associated with the at least one patient;

receiving, using the communication device, a notification when the at least one primary medical facility is ready to assist the at least one patient;

driving, using a transporter automotive vehicle, to the location of the at least one patient, and driving, using the transporter automotive vehicle, to the location of the primary medical facility associated with the at least one patient.

9. The method to facilitate provisioning of an emergency health service as claimed in claim 8 comprising:

providing, using a kiosk, at least one patient information associated with the at least one patient to the at least one primary medical facility;

receiving, using the communication device, at least one patient information; and transmitting, using the communication device, the at least one transportation information to the at least one transporter device associated with the at least one transporter.

10. The method to facilitate provisioning of an emergency health service as claimed in claim 9 comprising:

driving, using the transporter automotive vehicle, to the kiosk location associated with the at least one patient; and transporting, using the transporter automotive vehicle, the at least one patient from the kiosk location to the associated at least one primary medical facility.

11. A system to facilitate provisioning of an emergency health service comprising:

a communication device configured for:

receiving at least one patient information associated with at least one patient from at least one patient device;

transmitting the at least one patient information to the at least one medical facility device associated with at least one medical facility;

receiving at least one medical facility information from the at least one medical facility device;

transmitting the notification to the at least one patient device and at least one primary medical facility device associated with the at least one primary medical facility;

a processing device configured for:

analyzing the at least one medical facility information and the at least one patient information;

matching the at least one patient with at least one primary medical facility of the at least one medical facility based on the analyzing;

generating a notification based on the matched at least one patient and the at least one primary medical facility;

generating at least one transportation information associated with transportation of the at least one patient to the at least one primary medical facility based on the matched at least one patient and the at least one primary medical facility;

a storage device configured for:

storing at least one of the at least one patient information and the at least one medical facility information;

the processing device further configured for:

generating at least one waiting time information;

the communication device further configured for:

sending the at least one waiting time information to the at least one patient; and receiving the at least one waiting time information.

12. The system to facilitate provisioning of an emergency health service as claimed in claim 11 comprising:

the communication device further configured for:

receiving a number of appointments associated with the primary medical facility scheduled before the at least one patient;

sending the at least one waiting time information to the at least one patient; and the processing device further configured for:

updating the at least one waiting time information based on the number of appointments.

13. The system to facilitate provisioning of an emergency health service as claimed in claim 11 comprising:
   the communication device further configured for:
      transmitting the at least one transportation information to the at least one transporter device associated with at least one transporter; and
      receiving the transportation information associated with at the least one patient.

14. The system to facilitate provisioning of an emergency health service as claimed in claim 13 comprising:
   an automotive vehicle configured for:
      driving the at least one patient to the at least one primary medical facility;
   the communication device further configured for:
      checking the at least one wait time information associated with the at least one patient; and
      receiving a notification when the at least one primary medical facility is ready to assist the at least one patient.

15. The system to facilitate provisioning of an emergency health service as claimed in claim 13 comprising:
   a transporter automotive vehicle configured for:
      driving to the location of the at least one patient; and
      driving to the location of the primary medical facility associated with the at least one patient.

16. The system to facilitate provisioning of an emergency health service as claimed in claim 11 comprising:
   a kiosk device configured for:
      providing at least one patient information associated with the at least one patient to the at least one primary medical facility;
   a communication device further configured for:
      receiving at least one patient information; and
      transmitting the at least one transportation information to the at least one transporter device associated with the at least one transporter.

17. The system to facilitate provisioning of an emergency health service as claimed in claim 16 comprising:
   the transporter automotive vehicle further configured for:
      driving to the kiosk location associated with the at least one patient; and
      transporting the at least one patient from the kiosk location to the associated at least one primary medical facility.

* * * * *